(12) United States Patent
Halverson

(10) Patent No.: US 6,428,499 B1
(45) Date of Patent: *Aug. 6, 2002

(54) ULTRASONIC LIPOSUCTION DEVICE AND METHOD OF USING THE SAME

(75) Inventor: Kevin Halverson, Garden Grove, CA (US)

(73) Assignee: California Institute of Tissue Engineering and Instrumentation, LLC, Visalia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/587,781

(22) Filed: Jun. 6, 2000

Related U.S. Application Data

(63) Continuation of application No. 08/933,458, filed on Sep. 18, 1997, now Pat. No. 6,071,260.

(51) Int. Cl.⁷ .............................. A61B 17/20
(52) U.S. Cl. .................. 604/22; 604/542; 604/902
(58) Field of Search .................... 604/22, 35, 902, 604/27, 118–119, 121, 264, 523, 533, 534–535, 540–541, 181, 184; 606/128, 169, 170

(56) References Cited

U.S. PATENT DOCUMENTS

| 4,169,984 A | 10/1979 | Parisi |
| 4,173,725 A | 11/1979 | Asai et al. |
| 4,425,115 A | 1/1984 | Wuchinich |
| 4,428,748 A | 1/1984 | Peyman et al. |
| 4,504,264 A | 3/1985 | Kelman |
| 4,515,583 A | 5/1985 | Sorich |
| 4,531,934 A | 7/1985 | Kossovsky et al. |
| 4,886,491 A | 12/1989 | Parisi et al. |
| 4,978,333 A | 12/1990 | Broadwin et al. |
| 5,026,387 A | 6/1991 | Thomas |
| 5,151,084 A | 9/1992 | Khek |
| 5,181,907 A | 1/1993 | Becker |
| 5,263,957 A | 11/1993 | Davison |
| 5,348,535 A | 9/1994 | Cucin |
| 5,419,761 A | 5/1995 | Narayanan et al. |
| 5,484,398 A | 1/1996 | Stoddard |
| 5,486,162 A | 1/1996 | Brumbach |
| 5,505,693 A | 4/1996 | Mackool |
| 5,514,086 A | * 5/1996 | Parisi et al. |
| 5,516,043 A | 5/1996 | Manna et al. |
| 5,527,273 A | 6/1996 | Manna et al. |
| 5,569,178 A | 10/1996 | Henley |
| 5,628,743 A | 5/1997 | Cimino |
| 5,638,822 A | 6/1997 | Seyed-Bolorforosh et al. |
| 5,643,198 A | 7/1997 | Cucin |
| 5,665,101 A | 9/1997 | Becker et al. |

FOREIGN PATENT DOCUMENTS

EP 0269870 6/1988
WO 93/14709 8/1993

* cited by examiner

Primary Examiner—Brian L. Casler
Assistant Examiner—LoAn H. Thanh
(74) Attorney, Agent, or Firm—Benesch, Friedlander Coplan & Aronoff, LLP; Raymond A. Miller

(57) ABSTRACT

An ultrasonic liposuction device comprises a piezoelectric crystal transducer assembly that is connectable to a solid push rod that provides for the use of an interchangeable operative probe. The push rod is made of one material and the probe is made of a different material. The probe can be hollow, if aspiration of the fatty tissue is desired, or it can be solid.

4 Claims, 5 Drawing Sheets

ULTRASONIC LIPOSUCTION DEVICE AND METHOD OF USING THE SAME

CROSS-REFERENCE TO RELATED APPLICATIONS

This is a Continuation of U.S. Ser. No. 08/933,458 filed Sep. 18, 1997 which issued as U.S. Pat. No. 6,071,260 on Jun. 6, 2000.

BACKGROUND OF THE INVENTION

1. Field of the Invention

The present invention is directed to an ultrasonic liposuction device and a method of using the same to remove unwanted tissue or fat from a mammalia body. More particularly, the present invention is directed to an ultrasonic liposuction device which includes a push rod which vibrates at a predetermined frequency, and which in turn drives a probe or cannula at a predetermined frequency and amplitude in order to assist in the cavitation, emulsion and removal of fat tissue from a patient's body.

2. Background and Description of the Related Art

During the past 20 to 25 years, liposuction or "suction assistant lipectamy" has become a widely accepted procedure for removing localized areas of fat tissue which are normally unresponsive to diet or exercise. Regions of the body which are frequently treated by liposuction include: the waist ("love handles"); buttocks; thighs ("saddle bags"); ankles; lower legs; upper arms and the jowl area of the face. Liposuction has become a major source of revenue for the cosmetic industry. In conventional liposuction the removal of unwanted fat tissue is typically accomplished by inserting a narrow metal probe or cannula through an incision in the patient's skin and moving the probe back and forth within the patient's body to loosen the fat tissue. A vacuum is applied to suck out fat tissue that the cannula is in contact with. The procedure normally results in long tubular cavities in a wattle like pattern in the patient's fatty tissue area. The cannula generally has a rounded end and a small opening along the side or at the top in order to allow the fat particles to be removed. By manipulating the tube in and out of the area, a large amount of fatty deposit may be removed and the subject area is flattened, thereby approving the appearance the patient upon which the procedure is being performed.

Although the aesthetic benefits of conventional liposuction are well documented, the conventional procedure described above is normally very traumatic and usually accompanied by severe bruising of the treated area and the surrounding area. In fact, the bruising may be quite extensive due to the disruption of the small blood vessels which are attached to the fat globules being removed. Blood loss is also a concern for patients due to the fact that conventional liposuction devices are unable to differentiate between fat and connective tissue or blood vessels, the tissue is being ripped from the body was connective tissue and/or blood vessels.

In addition to the trauma to the patient, the physician generally uses a great deal of energy due to the force required to move the probe in and out of the area being treated. This force is necessary on the physician's behalf because the in and out movement of the probe shears off fat tissue particles. The fat tissue particles sheared off are drawn into the tube and out of the body by vacuum. The reason a blunt end probe or cannula is used is that the blunt end of the cannula pushes the larger blood vessels and nerves out of the way thereby causing less damage or trauma to the patient.

As can be seen above, conventional liposuction and the devices used therein have well documented undesirable side effects, including, unwanted trauma to the patient and physical exhaustion and tiring of the surgeon. In response to these disadvantages, ultrasonic lipectomy or liposuction procedures have been developed which rely on an ultrasonic transducer to vibrate the probe to reduce the effort of the surgeon and reduce the trauma to the patient. Generally, in these procedures the suction probe is connected to an electromechanical transducer of either magnetostrictive or electrostrictive design. Upon activation of the transducer longitudinal vibrations are sent up the probe and the distal end of the probe is turned into a vibrating wand which serves to liquefy (emulsify or cavitate) the fat that comes in contact with it either through heat (U.S. Pat. No. 4,886,491 which is hereby incorporated herein by reference in its entirety) or cavitation (U.S. Pat. No. 5,419,761 which is also hereby incorporated herein by reference in its entirety). The vibratory effect of the probe allows the surgeon to move the probe through fatty tissue very easily. The fatty emulsion or liquid that results from melting or cavitation is removed from the body, much in the same way as standard liposuction technique, that is, by way of as suction source and a collection bottle. The level of vacuum needed to remove the fat from ultrasonic liposuction is substantially less than that needed in the standard liposuction procedure due to the fact that the fat is liquefied or emulsified. The liquification of the fatty tissue surrounding the distal end of the probe allows the probe to be easily inserted and retracted from the body, and as a consequence reduces the trauma to the patient and reduces the effort needed by the surgeon. Obviously one of the benefits of ultrasonic liposuction is less fatigue on the part of the surgeon which allows him to be more efficient and more alert and allows him to perform more procedures in a day. In addition, less bleeding has been seen during the use of these procedures and the ultrasonic vibration of the probe has shown to have a cauterizing effect on small blood vessels.

U.S. Pat. No. 5,527,273 and U.S. Pat. No. 5,181,907 both of which are hereby incorporated by reference in their entirety outline several of the advantages offered by ultrasonic liposuction. Ultrasonic liposuction devices developed to date require cannulas or probes which are specifically designed to resonate or translate at desired frequencies. The probes are vibrated at ultrasonic frequencies in the range of 16,000 to 60,000 cycles per second. Therefore, the probes that are being used are subject to stresses and fatigues not encountered by passive probes used in conventional liposuction procedures. Additionally, the ultrasonic liposuction probes generally must be designed to provide sufficient multiplication of the amplitude input provided by the transducer which drives it.

It is known that a particularly effective probe for ultrasonic liposuction is a hollow cylindrical probe with a bullet shaped tip on the distal end. The tip can be welded or otherwise affixed to the probe. Both probe and tip can be manufactured from a variety of acoustically conductive metals, including cold-rolled steel, titanium and aluminum. In presently known devices, the probe and tip are manufactured from the same materials, or from very similar materials, to ensure effective propagation of the ultrasonic waves all the way to the tip of the probe. Propagation of the waves to the distal tip of the probe is desirable, because this causes the tip of the probe to be able to melt and emulsify fat, facilitating insertion of the probe into the fatty tissue.

However, there is a disadvantage sometime associated with an ultrasonic probe having an acoustically conductive tip. For instance, when the probe has been inserted into the fatty tissue near the skin or the peritoneum, resistance can be met. When resistance is met, the wattage at the tip increases, and it can increase to the point of damaging the skin or the peritoneum. During such manipulations, the heat generated at the tip of the probe may be in excess of the heat reasonably required for the melting of fat. In other words, if care is not exercised, the tip may be hotter than it needs to be, and the result can be burning of tissues, damage of muscles or blood vessels, and even penetration of membranes, such as the skin or the peritoneum. Therefore, while the bullet shaped tip of acoustically conductive material, it can be very beneficial during penetration, it can under certain circumstances, also be detrimental.

Relying on the probe as the vibrational element to transmit the vibration or multiply the vibration provided by the input acoustical source also results in numerous disadvantages when performing ultrasonic liposuction. Straight cylindrical probes normally do not provide gains for ultrasonic vibration and accordingly, the probes must be driven at the high input amplitudes necessary for tissue liquefaction. This causes high stress concentration at node points or points where the vibratory motion and the standing wave are zero. When stress is high, material heating problem can occur. The problem is that the temperature of the probe at the stress know points elevates and again can cause tissue burning or charring when in contact with the tissue of the body or the patient in which the liposuction application is being performed. Obviously, this major drawback of using laboratory elements must be avoided since the probes are inserted deeply in the body and burning or scarring of the lower levels epidermis or other tissues or organs may result.

In practice, the probes described heat significally at the nodal regions and are prone to fracture at high amplitudes and have a tendency to break into transverse motion wherein the tips of the probes causing fracturing and the possibility of leaving pieces of metal in the body of the patient in which the operation is being performed.

The necessity to construct the probe out of a material which transmits the vibratory amplitude of the electromechanical transducer also provides a number of disadvantages to a field of ultrasonic liposuction. Generally, the probes are limited in construction a titanium or titanium alloy due to the expansion/contraction characteristics of titanium and can be very fragile in design in that a risk of loss of amplitude or frequency may occur with minor probe damage such as scratching or general wear so that the vibrational frequency of the probe is out of tune of that desired or indicative by the electromechanical transducer. Additionally, the working end of the probe must be larger than the body of the probe in order to accommodate the aspiration channel and maintain the ultrasonic resonance.

OBJECTS OF THE PRESENT INVENTION

An object of the present invention is to provide an improved device for removal of tissue.

Another object of the present invention to provide an ultrasonic liposuction device which does not suffer from the disadvantage of having a probe which becomes too hot.

Another object of the present invention is to minimize the need for expansion and contraction of the probe which in turn minimizes the need for nodes.

A further object of the present invention to provide an ultrasonic liposuction device which may utilize interchangeable probes to facilitate different types of probe manipulations.

It is still further object of the present invention to provide an ultrasonic liposuction device which is easy to use and economical to manufacture.

Another object of the present invention is to provide a device which minimizes injury to nerves and blood vessels and overall trauma during a liposuction procedure included reduced blood loss.

Another object of the present invention includes providing liposuction device which minimizes trauma and which yields a more even reshaping of overlaying skin surfaces than conventional procedures and allows the surgeon to know how much and where the fat that is being removed is coming from.

Another object of the present invention is to provide an ultrasonic liposuction device which is designed to allow interchangeable probes to be used which do not require specialized design or tuning.

Another object of the present invention is to allow probes other than those constructed of titanium or titanium alloy such as carbon fiber or various aluminum alloys to be used while obtaining benefits of using the convention probes described of the related art.

Another object of the present invention is to provide a durable ultrasonic liposuction device which is usable even after general wear and which is not affected by scratches and minor abrasions to the probe which occur during the normal course of liposuction.

Another object is to provide an ultrasonic liposuction device which includes a probe have a large lumen so that high volume aspiration may be utilized to speed the evacuation of soft tissue and thus decrease the surgery and anesthesia time in a liposuction procedure.

Another object of the present invention is to increase the surface area of the suction apparatus by increasing the number of holes in communication with the fat and inner lumen of the probe.

Another object of the present invention is to utilize curved probes and probes of a variety of sizes and shapes, the probes being substantially independent of the transmission properties of the probe.

Another object is to allow to provide a ultrasonic liposuction device whereby the frequency of the probe can be controlled by the user.

These and other objects of the present invention will be apparent from the drawings and detailed description contained herein.

SUMMARY OF THE INVENTION

An ultrasonic probe for removing tissue from a human being or other animal, particularly for removing fatty tissue, comprises a handpiece housing containing a piezoelectric crystal transducer, a push rod which is formed of titanium or stainless steel releasably secured to the housing and a probe formed of substantially any material and being any size is removably attached to the distal end of the push rod. It should also be noted that the probe can be solid, rather than hollow, if aspiration of the melted fatty tissue is not required. If the probe is hollow, it can have a lateral opening for aspiration, or there could be an opening through the tip of the probe.

The piezoelectric crystal assembly comprises several disc-shaped piezoelectric crystals, each having a central bore. The crystals are mounted in line with each other within the handpiece housing. The crystals extend along a portion of the outer surface of the rod, so that there is efficient energy transfer between the crystals and the push rod through the changeover. The handpiece housing is formed of a material such as metal and comprises a central cylindrical member.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENTS

Figure 1:
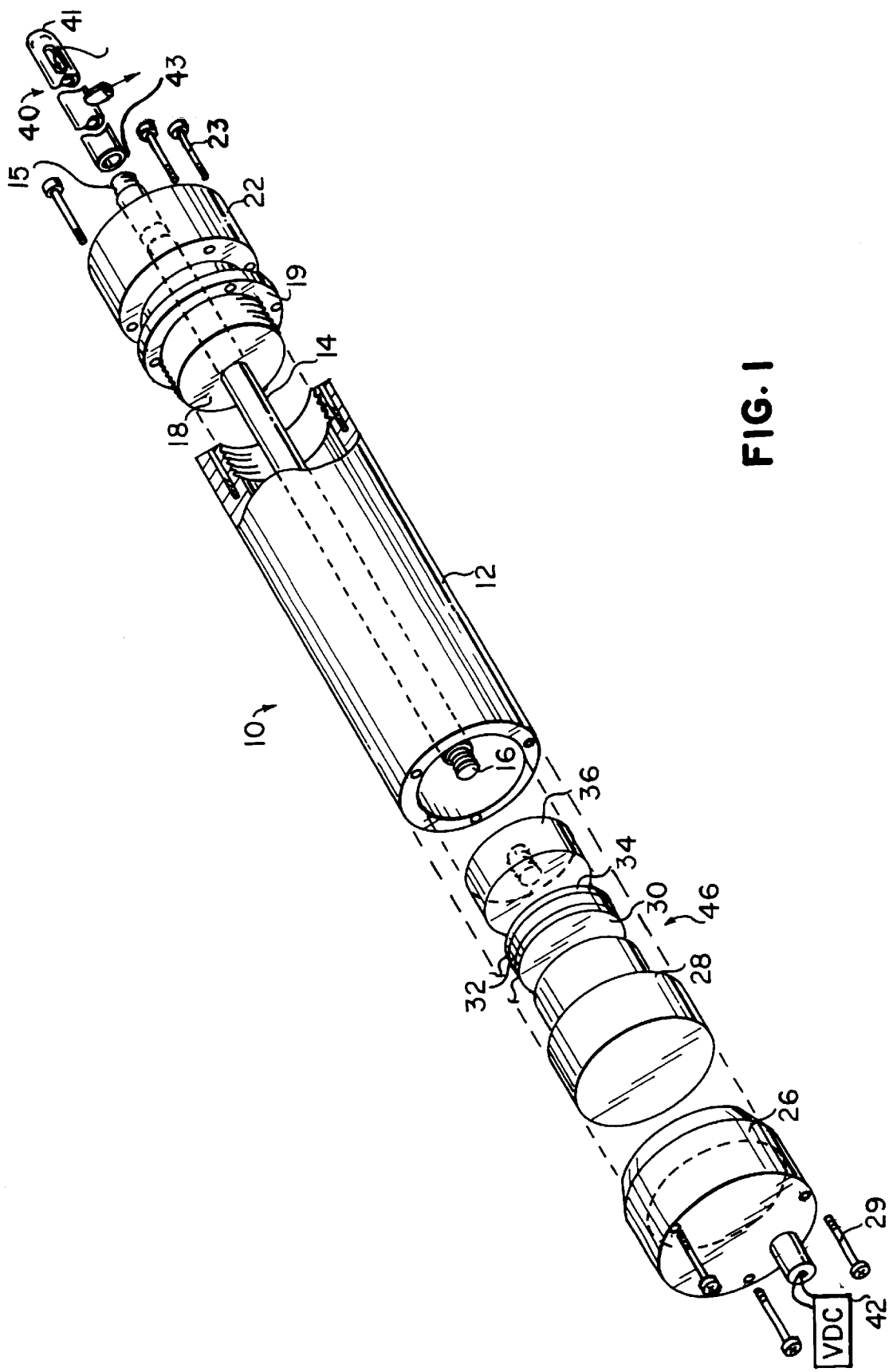
FIG. 1 is an exploded perspective view of a preferred embodiment of the present invention.
Figure 2:
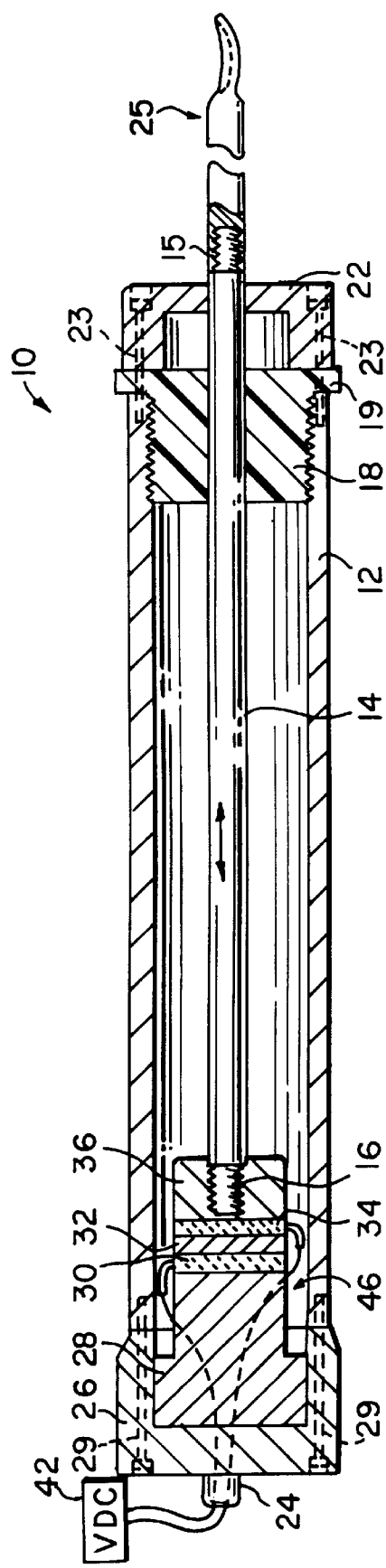
FIG. 2 is a cross sectional view of the preferred embodiment of the present invention.
Figure 3:
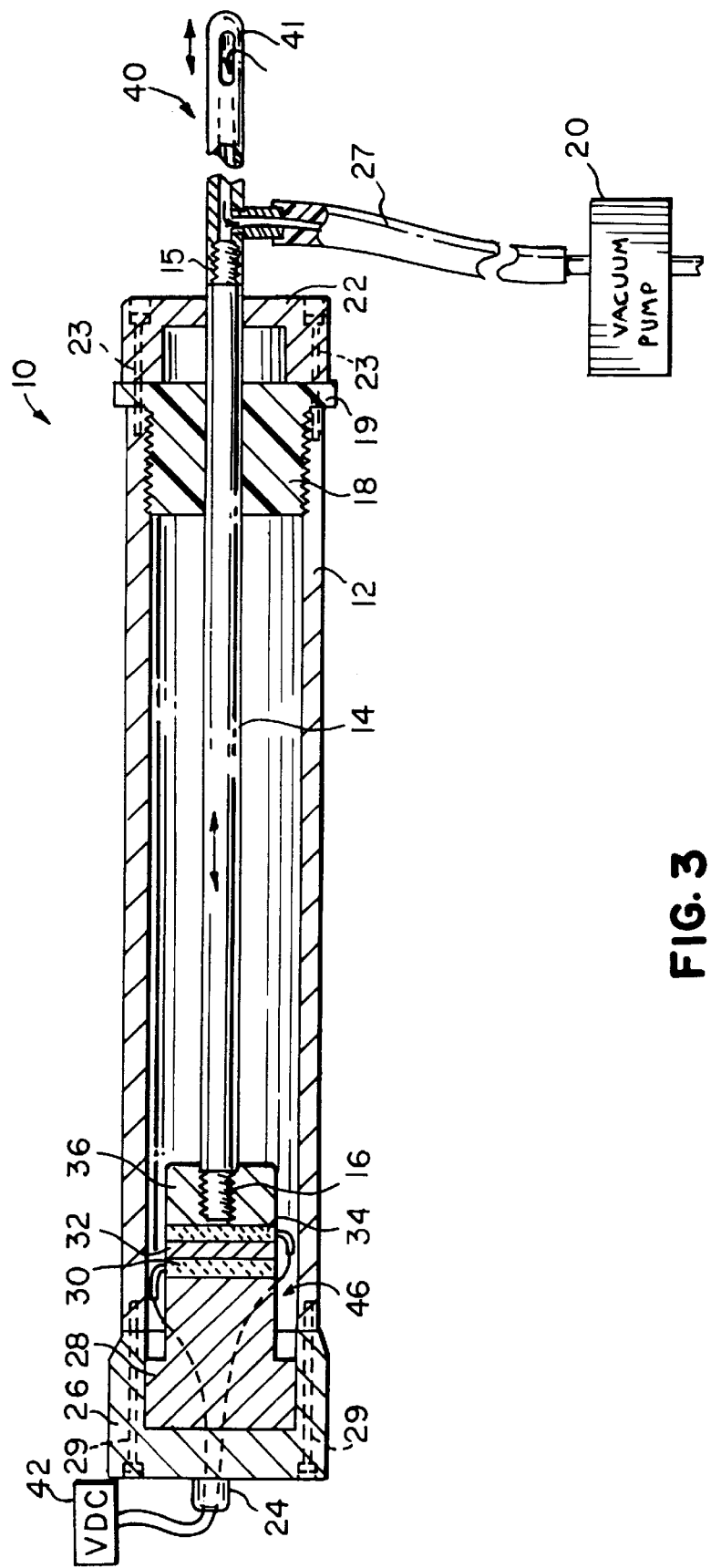
FIG. 3 is an exploded perspective view of an alternative embodiment of an alternative embodiment of the present invention.

With reference now to FIGS. 1 and 2, an ultrasonic liposuction device 10 used for ultrasonically removing fatty tissue is illustrated according to the present embodiment of the invention and includes a handpiece or housing 12 which houses piezoelectric transducer motor stack 46 for providing ultrasonic vibrations to push rod 14. Push rod 14 which has a proximal end 16 is typically attached to motor stack 46 at its proximal end 16 and a distal end 15 which extends through bushing 18. Push rod 14 is the mechanical connection of probe 40 and the piezoelectric transducer of motor stack 46.

Motor stack 46 is comprised of a tin plated copper disk 28 fixably attached to a first ceramic piezoelectric crystal 30 which is itself attached to a copper disk 32 and subsequently attached to a second ceramic piezoelectric crystal 34. Finally, motor stack 46 includes a second tin plated copper disk 36 which is designed to threadingly receive proximal threaded end 16 of the push rod 14. The motor stack 46 is electrically connected through connector 24 to a source of electrical energy shown schematically as 42. When electric current is supplied from the source of electrical energy 42 to the motor stack 46 through the connector 24 the motor stack, more specifically the piezoelectric crystals 30 and 34 vibrate back and forth at the desired frequency. The frequency supplied to the push rod 14 can vary in the range of 6,000 to 60,000 cycles per second depending on the intended use. It is preferable that the range of frequency be between 20,000 and 30,000 cycles per second and more preferably 22,000 to 25,000 cycles per second for the removal of fat tissue without unwanted burning or trauma. The motor stack 46 may be comprised of any vibrational element, but is preferably a piezoelectric transducer like those described in U.S. Pat. No. 5,514,086 which is hereby incorporated by reference in its entirety and U.S. Pat. No. 5,638,822 which is also hereby incorporated herein in its entirety by reference. A high frequency source of alternating voltage 42 is supplied to the motor stack 46 through an opening in the rear cap 26 of the housing 12.

With an alternating voltage of an ultrasonic frequency applied, the piezoelectric crystals 30 and 34 vibrate in a known manner at the ultrasonic frequency. The frequency is in the range of 20 KHz to 65 KHz and it is preferably approximately 20 to 40 KHz most preferably in the range of 22.5 to about 25 KHz. The amplitude of the ultrasonic vibration is from 0 to 0.0015 inch, and preferably approximately 0.0002 to 0.005 inch which preferably translate to no greater than about 500 microns when measured at the tip, even more preferably less than about 250 microns at the tip and even more preferably in the range of about 5 microns to about 125 microns (0.0002 to about 0.005 inch) when measured at the tip. The crystals are mechanically coupled to push rod 14. Push rod 14 translates the ultrasonic vibrations generated at the crystals 30 and 34 to the proximal end 43 of the probe 40.

The probe 40 generally has a smoothly contoured outer surface which is substantially symmetrical about its longitudinal axis of ultrasonic liposuction device 10. The probe 40 is preferably made of surgical or stainless steel but may in some cases be made of hard plastic and can take on a number of a variety of shapes and is not necessary for the probe 40 to have or be constructed of a vibrational element. This feature is one of the more flexible aspects of the present invention. Since the present invention does not require the probe to be constructed of a resonating a metal such as titanium or vanadium, the probe 40 can be shaped in essentially any size or desired design criteria which satisfies the intended liposuction use. The probe 40 may be slightly tapered toward the distal end. The probe 40 can be of of any length but is generally from about 5 cm to about 40 cm depending upon its intended use. For example, a cannula probe 40 of about 30 cm in length might be prepared for large areas such as the buttocks while a small bicentimeter probe 40 is preferred for facial surgery. Probe 40 can be made of, among other things, aluminum, carbon fiber, plastic, and surgical stainless-steel and may include 45.degree. angles in the probe or contain a flat end to function as a "bloodless knife". The diameter of the probe 40 can also vary and is typically in the range of 5 to 25 mm preferably slightly tapered with the smaller diameter of the distal end of the probe 40. Normally, the distal end 41 of the probe 40 is rounded or bullet shaped and approximates a hemisphere. The distal end 41 of the probe 40 is preferably shaped in this way in order to effectively push large blood vessels and nerves out of the way to one side or the other to reduce trauma to the patient and reduce loss of feeling and excessive loss of blood. The proximal end 43 of the probe 40 threadingly engages the distal threaded end 15 of the push rod 14 and may include a slit indented area that is adapted to receive a rubber hose 27. The rubber hose 27 connects the probe 40 to a source of vacuum shown schematically at 20. The outside of the housing 12 functions as a grip area for the surgeon to place his hand and is separated from the push rod 14 via bushing 18. Bushing 18 functions as a bearing for push rod 14 and is preferably self lubricating, the preferred design choice being manufactured out of Teflon®. The proximal end 16 of the push rod 14 is threadingly engaged by the motor stack 46 whereby the piezoelectric crystals 30 and 34 function to vibrate the push rod 14. The push rod 14 is generally formed of a titanium or vanadium material whereby the vibration frequency generated at the motor stack 46 is translated through the push rod 14 to distal threaded end 15 of the push rod 14. The push rod 14 may be selectively manufactured in an order to function to multiply and increase the frequency of the vibration generated in the motor stack 46 or simply transform the vibrational energy of the piezoelectric crystals 30 and 34.

Front cap 22 is rigidly attached to the housing via bolts 23 which secure the front cap to the housing with the flange 19 of bushing 18 being disposed between the front gap 22 and the housing 12. Similarly, rear cap 26 is fixedly attached to the rear portion of the housing 12 via bolts 29 which mount the rear cap to the housing 12.

The ultrasonic liposuction device 10 of the present invention and the method of using the ultrasonic liposuction device 10 of the present invention has several important advantages over the standard medical practice of fat removal or liposuction and over liposuction wherein the ultrasonic probe is required to resonate from the frequency provided from the motor stack 46. The present invention substantially reduces the injury to nerves and considerably reduces bleeding and produces a smoother and more even surface than punching holes. The device also eases the labor of moving the probe 40 by the surgeon since cavitation or emulsification is doing substantially all the work and pressure, twisting, speed of physical movement by the surgeon and scraping are not necessary. The new method and device shortens the surgical time and there is reduced tearing stretching or heating of the tissue and no removing of chunks of tissue either due to cutting or high suction pressure. The liquid material aspirated by the pump also flows easily since there are few particles or pieces of fat. FIG. 2 illustrates an alternative embodiment of the present invention whereby the probe 25 is not hollow but rather solid with a spatula shaped end which may be useful in scraping of fat material either in conjunction with or separate from the ultrasonic aspects of the method.

One of the more novel features of the present invention is that the push rod 14 which is normally constructed out of acoustic material is substantially protected from damage due to the fact that it is housed almost entirely within the housing 12, bushing 18, and front cap 22. Thus the useful life of the liposuction device 10 is extended and the durability of the liposuction device 10 is increased.

Figure 4:
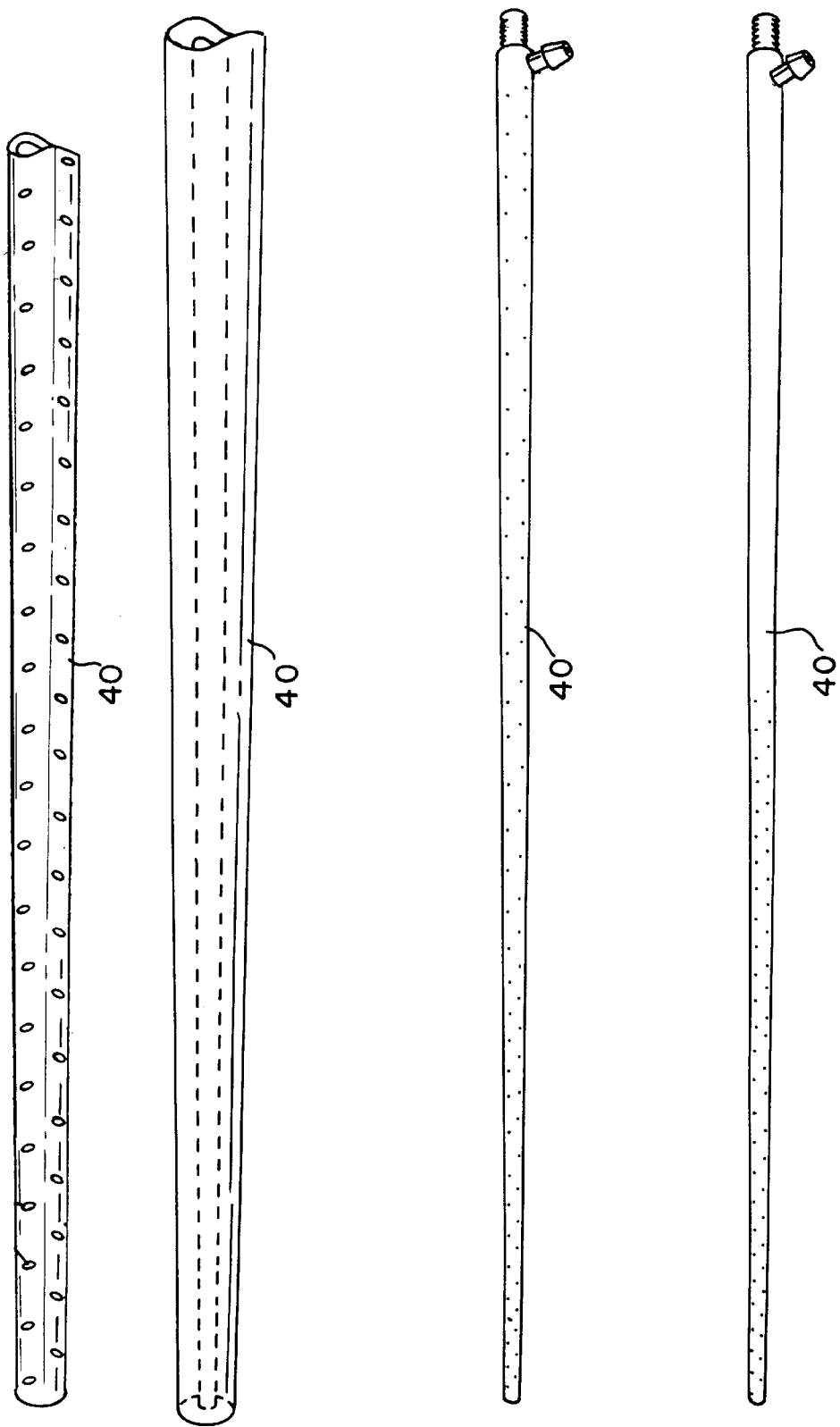
FIG. 4 is a perspective view of alternative probes that may be used in conjunction with the present invention.
Figure 5:
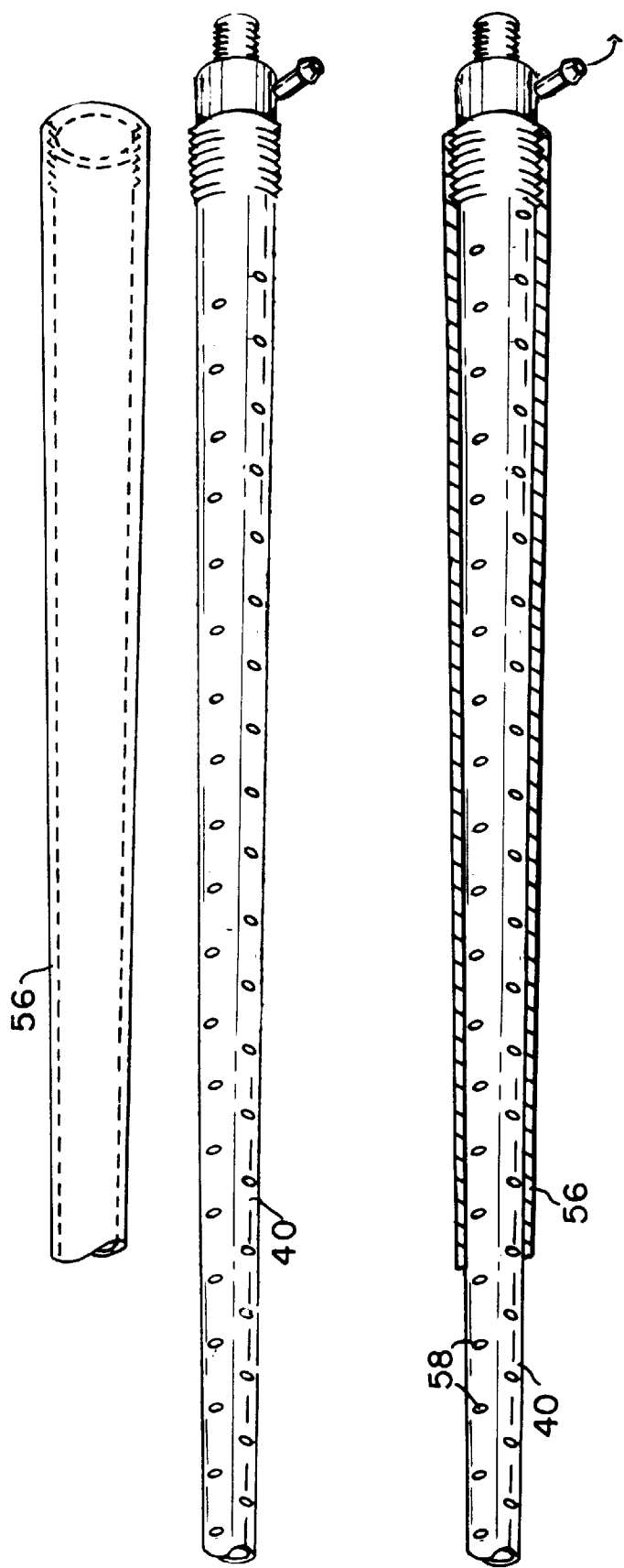
FIG. 5 is a perspective view of alternative probes with a sleeve covering various lengths of the aspirating.

FIG. 4 and FIG. 5 illustrate alternative probes 40 which may be used with the present liposuction device 10. As illustrated the probes 40 may have holes 58 through which the emulsified or liquefied fat may be removed. The probe 40 having holes 58 may also include a sleeve 56 which may be threadingly secured to the probe 40. The sleeve 56 allows the vacuum to be selectively applied to the desired areas. The sleeve 56 may fit tightly over the probe 40 or may fit loosely whereby the probe 40 could the be solid and liquified or emulsified fat could be withdrawn in the space between the probe 40 and the sleeve 56.

Although the invention has been described in terms of particular embodiments in an application, one of ordinary skill in the art, in light of this teaching, can generate additional embodiments and modifications without departing from the spirit of, or exceeding the scope of the claimed invention. Accordingly it is to be understood that the drawings and the descriptions herein are proffered by way of example only to facilitate comprehension of the invention and should not be construed to limit the scope thereof.

What is claimed is:

1. A device for removal of fatty tissue comprising:
   an ultrasonic generating means;
   a solid monolithic push rod having a proximal and distal end in communication with said ultrasonic generating means, said push rod is constructed of a first material; and
   a probe for removal of fatty tissue attached to said push rod at the distal end thereof wherein said probe is hollow defining an interior space and an exterior surface, said probe is constructed of a second material that is different from said first material.

2. The device of claim 1, wherein said probe includes at least one aperture in fluid communication with said interior space.

3. The device of claim 2, wherein said probe includes an outlet port in fluid communication with said interior space.

4. The device of claim 3, further comprising a suction means operatively connected to said outlet port for aspiration of fatty tissue.

\* \* \* \* \*